United States Patent [19]

Sperrazza

[11] 4,160,599
[45] Jul. 10, 1979

[54] OPTICAL GAGING SYSTEM

[75] Inventor: Joseph L. Sperrazza, New Haven, Conn.

[73] Assignee: Universal Technology, Inc., Woodbridge, Conn.

[21] Appl. No.: 858,822

[22] Filed: Dec. 8, 1977

[51] Int. Cl.² .............................................. G01B 11/06
[52] U.S. Cl. ..................................... 356/381; 250/560
[58] Field of Search ............... 356/156; 250/559, 560, 250/214 AG, 214 AL, 214 B, 214 C; 358/211, 212, 213

[56] References Cited

U.S. PATENT DOCUMENTS

| | | | |
|---|---|---|---|
| 3,565,531 | 2/1971 | Kane | 356/156 |
| 3,632,226 | 1/1972 | Filby et al. | 250/559 |
| 3,667,846 | 6/1972 | Nater et al. | 356/156 |
| 3,835,313 | 9/1974 | Stiefelmeyer et al. | 250/214 C |

Primary Examiner—John K. Corbin
Assistant Examiner—R. A. Rosenberger
Attorney, Agent, or Firm—DeLio and Montgomery

[57] ABSTRACT

An electro-optical gaging system which comprises a linear array of photo-sensitive diodes where the thickness of an object against a dark background is measured by determining the number of diodes which are discharged due to light incident thereon from the object. Each diode of the array is sequentially scanned during a scanning cycle to recharge the capacitance of the discharged diodes and the number of charging pulses is a measurement of the thickness of the object. A separate photo-sensitive element senses the light conditions and generates pulses which determine the repetition rate of the scanning cycle to maintain system calibration. A start scan signal is also utilized to determine that the light intensity is within predetermined limits.

6 Claims, 8 Drawing Figures

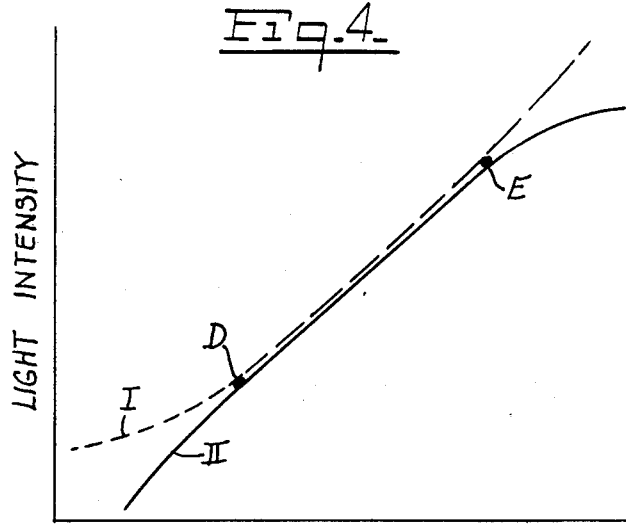
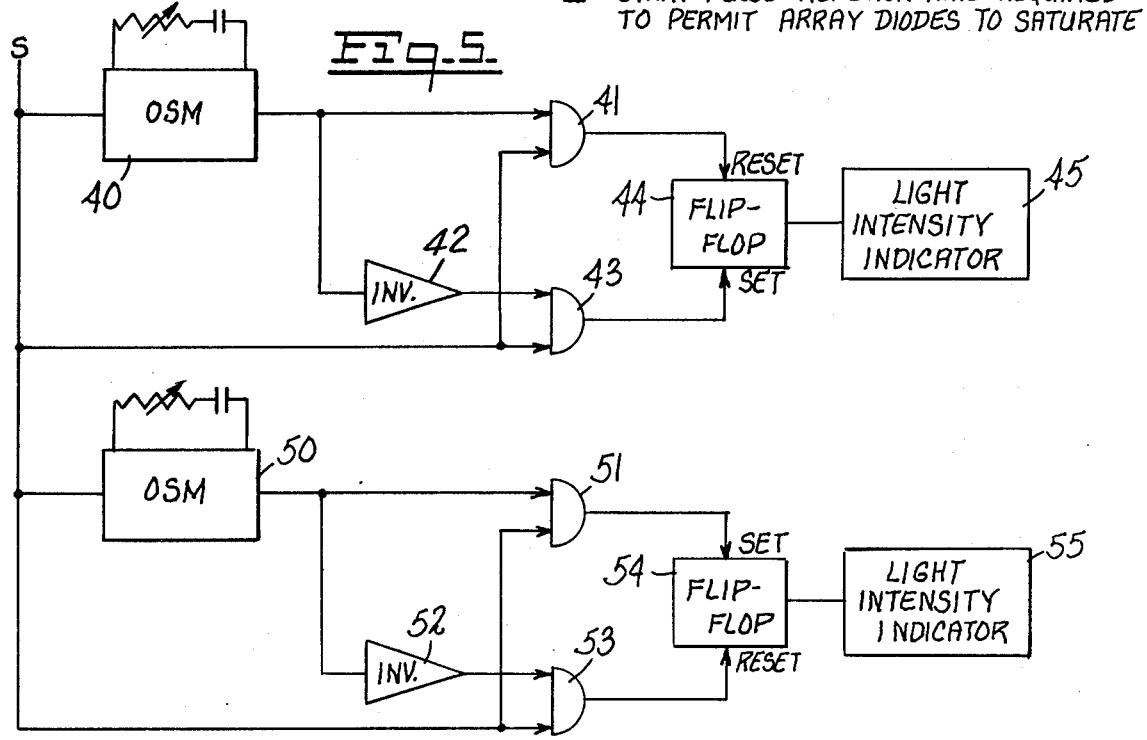
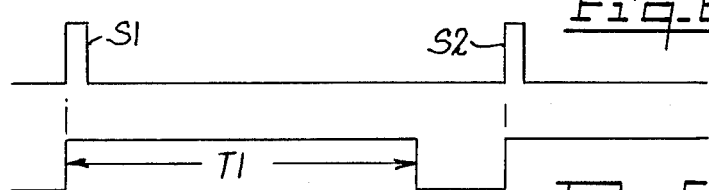
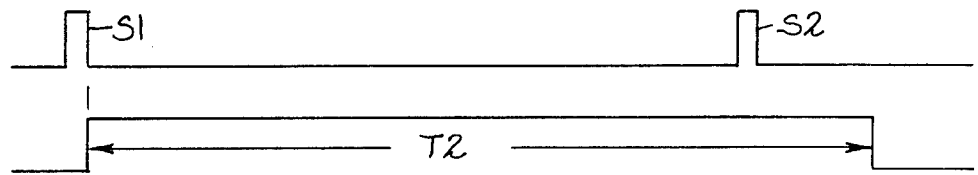

OPTICAL GAGING SYSTEM

This invention relates to gaging devices, and more particularly relates to photo-sensitive electrical gaging devices on which an object may be imaged across an array of such photo-sensitive electrical elements to determine the thickness thereof.

It is well known in the electro-optical gaging art to image strip material across a linear array of photo-sensitive elements which measure a dimension of incident light from the strip or, alternatively, the dimension of occluded light against a lighted background.

In some cases the intensity of light emitted or reflected from the strip material may vary with time or other conditions. An example is drawn wire which, due to its heat, emits infra-red. Depending on the speed of draw, the possibility of line stoppages, etc., the amount of infra-red may vary leading to a calibration problem in the gaging system. The same problem, may occur in the reverse system where the background is lighted and the light may not be capable of precise regulation.

A typical photo-sensitive array comprises a linear array of equally spaced photo-sensitive diodes together with an associated switch of each diode. The diodes are back biased and have an inherent parallel capacitance. Each time the array is scanned, the switches are sequentially closed and the diode capacitance is charged. The capacitance discharges through the back-biased diode as a function of light intensity incident on the diode. The diodes may be considered as equivalent to variable resistances which provide a discharge path for the capacitance. The time of discharge therefor varies as a function of the incident light. When an object is imaged on the array, the light emanating or reflected from the object will render some diodes conductive, thus producing capacitive discharge. Then, during the next scanning cycle, as the diodes are sequentially interrogated, the number of charging pulses are counted. This count is then indicative of the thickness of the object imaged on the array.

Since the capacitance discharge time varies with incident light intensity, a scan cycle should not be initiated until sufficient time has passed for the capacitance to discharge.

Accordingly, the present invention provides a new and improved means of maintaining calibration of an electro-optical gaging system of the type described in which the repetition rate of initiation of a scan is carried as a function of sensed light intensity.

The present invention may be embodied in a system in which photo diodes discharge associated capacitors as a function of incident light. More time is required to discharge the capacitor as the intensity of the light decreases. Then, the overall cycle of operation of the system must be varied to accommodate the increased time cycle of operation. A separate photo-sensitive device is provided to sense the light intensity and control the initiation of the cycle time of scan of the array, and maintain calibration of the system. The invention further provides new and improved means for indicating when the light intensity is beyond acceptable upper and lower limits.

An object of this invention is to provide a new and improved electro-optical gaging system of the type described in which the frequency of initiation of a scanning cycle is made a function of the light intensity.

Another object of this invention is to provide a system of the type described having new and improved means for determining that the intensity of the light incident on a diode array of the type described is within acceptable limits.

The features of the invention which are believed to be novel are particularly pointed out and distinctly claimed in the concluding portion of this specification. The invention, however, both as to its organization and operation, together with further objects and advantages thereof may best be appreciated by reference to the following detailed description taken in conjunction with the drawings, wherein:

FIG. 4 is a graphical representation of the relationship of light intensity through the lens of the camera of FIG. 2 and the scanning repetition rate of the diode array;

FIG. 5 is a diagram, partly schematic and partly in block form, of a network for determining that the light passing the lens is within predetermined limits; and FIGS. 6a and 6b are diagrams of waveforms appearing in the network of FIG. 5.

Figure 1:
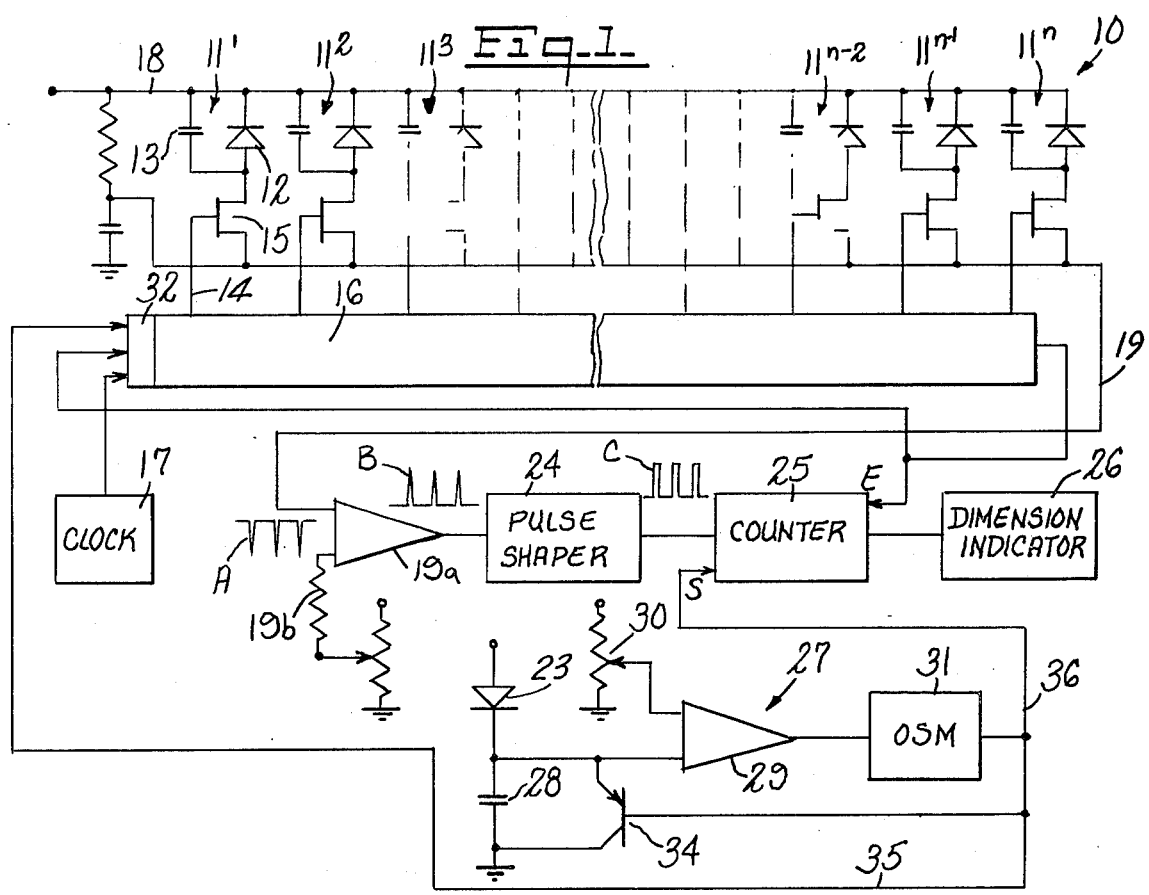
FIG. 1 is a diagarm, partly schematic and partly in block form, of a newtork which embodies the invention.

FIG. 1 exemplifies a typical linear array 10 of photo-sensitive diodes and accompanying circuitry, termed cells. Each cell $11^l$ to $11^n$ includes a back-biased photo-sensitive diode 12 having an inherent capacitance 13 which is effectively in parallel. Each cell is connected to an output line 14 which is at virtual ground through a switch shown as a transistor 15. The switches are serially turned ON and OFF by an address register in the form of a shift register 16. The address register is driven by two-phase clock pulses from a clock frequency generator 17 with a start pulse S initiating each interrogation or scanning cycle. Between scanning cycles the charge on each capacitance 13 decreases as curent discharges through its diode 12. This current is a function of the light intensity incident on the diode and the diode sensitivity. The loss of charge is replaced during each scan cycle when the capacitances are recharged by completing a circuit between positive line 18 and output line 19. A charge pulse appears as each cell is interrogated by the address register closing its associated switch, transistor 15. Such pulses are porportional to the light intensity of each diode and the leakage current, or otherwise stated the total discharge of the capacitor. The charging pulses supplying only dark leakage current are very small compared to those recharging the capacitances and may be amplitude discriminated. Then, by counting the charge pulses during each scan cycle, the width of an object imaged on an array of diodes of known uniform spacing may be determined. The pulses appearing on line 19 are supplied to a current amplifier 19a, and those pulses representative of recharging pulses A, due to light incident on diodes and above a threshold as may be set by a potentiometer 19b, are amplified to pulses B and may thereafter be shaped to rectangular pulses C.

Figure 2:
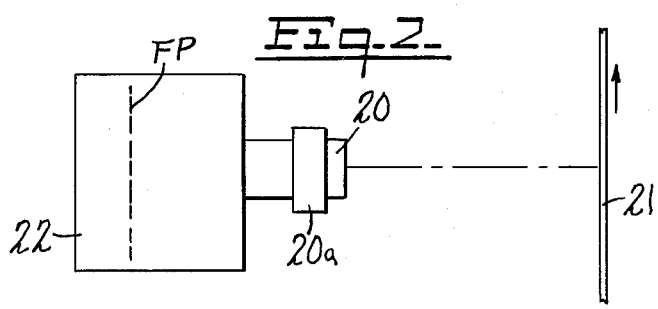
FIG. 2 is a diagrammatic view of a camera and gaged strip material.
Figure 3A:
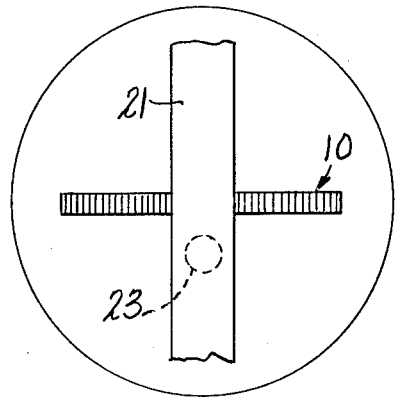
FIGS. 3a and 3b are representative views of a linear photo-diode array with the strip material imaged thereon.
Figure 3B:
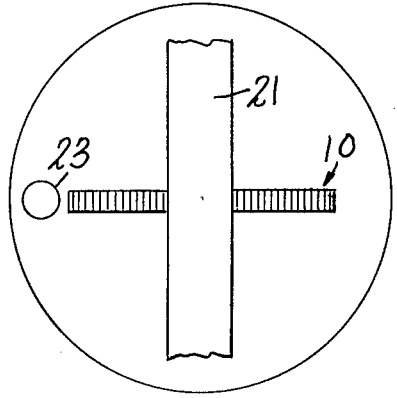

The present invention utilizes a system as thus far described in FIG. 1 in conjunction with a lens 20 (FIG. 2) to image a moving strip 21 on the array 10. The array 10 is placed in a camera-like housing 22 at the focal plane FP of lens 20. The lens 20 will include an aperture adjusting ring 20a. As shown in FIG. 3a, the strip 21 moves substantially perpendicular to the linear array 10. Another photo sensor 23 is positioned on the line of the strip to sense the light emanating or reflected therefrom. If the strip is dark and the background light, sensor 23 is positioned outside of the path of the strip to read the background light as shown in FIG. 3b. Sensor 23 may also be utilized with another lens to sense the light intensity of the strip at a location remote from lens 20.

Referring back to FIG. 1, the rectangular pulses shaped by pulse shaper 24 from the output of amplifier 19a are applied to a pulse counter 25 between the occurrence of a start scan pulse S, and an end of scan pulse E received as the overflow puse from the address register. The number of pulses counted by pulse counter 25 are indicative of the dimension of strip 21. This count is connected to a visual display or an indicator 26. If the gaged thickness departs from acceptable dimensions, suitable corrective measures may be taken on the processing line.

In the case of gaging a dark object against a light background, counter 25 is arranged as a down counter.

In accordance with one aspect of the invention, the initiate scan pulses S are generated at a rate proportional to the intensity of the light sensed from the strip 21 (FIG. 3a) or the background light (FIG. 3b).

A network 27 including sensor 23 generates start scan pulses S at a rate proportional to the sensed light intensity. A capacitor 28 is charged through sensor 23 in the form of a photo-sensitive diode. The rate of charging current to capacitor 28 is a function of the light incident on sensor 23. Sensor 23 acts as a light responsive variable resistance. When the potential on capacitor 28 reaches a predetermined value above that set on a level detector 29, as exemplified by a reference voltage from a potentiometer 30, detector 29 fires a one-shot multivibrator OSM 31. The output of OSM 31 provides the initiate scan pulse S. Pulse S applied to a start gate 32 in register 16 initiates a scan cycle by permitting the clock pulses to sequentially close the switches 15 and sequentially recharge the capacitances 13 of cells $11^l$ to $11^n$. When the end of scan pulse E appears, start gate 32 is closed. Then, the next scan cycle will not begin until the next start pulse S. During the interim between scan cycles, the capacitances 13 will discharge through associated diodes 12 as a function of the light incident on the diodes. Such discharge will be more rapid if the incident light intensity is high, and correspondingly less rapid if the incident light intensity is low.

Since the repetition rate of cycle initiator signals S is a function of the sensed light intensity, sufficient time is provided for capacitor discharge as a function of light intensity.

Concurrently with initiating a scan cycle, the start pulse S turns on transistor 34 to discharge capacitor 28, and initiates another light intensity measuring cycle over line 35 and also enables counter 25 over line 36.

The cycle repetition rate is thus proportional to sensed light intensity. With greater light intensity the capacitances of the diodes will discharge quicker, permitting a higher repetition of scanning cycles and vice versa.

Instead of the circuit 27, other networks which provide pulses at a repetition rate proportional to light intensity may be utilized. A satisfactory packaged system is one marketed by IPI, Integrated Photomatrix, Inc. of Mountainside, New Jersey, under the designation of IPI 13.

FIG. 4 is a graphical representation of the relationship between light intensity and (I) Start Scan pulse repetition rate and also (II), the Start Scan pulse rate required to permit the array diodes to saturate between scanning cycles. It will be noted that these two curves have a linear relationship between the points D and E, and diverge prior to D and subsequent to E. The curves are shown as substantially coincident, but in practice may be slightly separated. If the light intensity falls below point D, the diodes may not have sufficient time to discharge their respective capacitors between scanning cycles and a similar situation may occur beyond the point E. If this occurs, the amplitude of the charging pulses may not be sufficient to be detected by amplifier 19.

Accordingly, the system provides new and improved means for indicating when the sensed light is outside of limits necessary for proper calibration and operation of the system.

FIG. 5 exemplifies a circuit which is utilized to determine that the light intensity is within predetermined limits. The start pulse S is applied to a one-shot multivibrator OSM 40 which is preset to provide an output pulse T1 of a duration which is selected in accordance with the system. OSM 40 is connected to trigger on the leading edge of scan pulses S. Upon occurrence of a start pulse S1, OSM 40 will generate an output waveform T1, FIG. 6a, which is applied to a gate 41, and also inverted by an inverter 42 and then applied to a gate 43. If a second start pulse S2 should occur during the duration of the T1 pulse, gate 41 will apply a reset signal to a flip-flop 44. This indicates that the light intensity is not adequate; that is, above the point E on the curves of FIG. 4. This further indicates the repetition rate of the start scan pulse S is too high for the system even though the light intensity is high enough to give a fast discharge rate between scans. If, however, the pulse S2 should occur after the duration of OSM pulse T1 (FIG. 6a), Nand gate 43 will provide an output to set flip-flop 44 which will turn ON an indicator 45, which may be in the form of a light emitting diode. Flip-flop 44, once set, will remain set so long as there is no resetting pulse from gate 41. If the indicator light goes OFF, this indicates that the rate of the start pulse S is too high for the saturation current level of the array diodes.

This may be corrected by taking one of several measures. In the case where the strip is dark against a light background, the intensity of the background light may be decreased or the lens aperture decreased. If the light emanating or reflected from the strip is being measured, then the aperture of the lens may be decreased by means of the aperture adjustment 20a, FIG. 2.

The duration of the output of OSM 40 will be selected in accordance with system parameters and particularly the time for discharge current saturation of the diodes in the array. So long as the start pulse subsequent to the previous start pulse which triggered OSM 40 does not occur within the time duration of the output of OSM 50, the system will be operating below the point E. If the indicator 55 should go out, this will indicate too great a light intensity. Then, suitable correction measures may be taken, as previously described.

A similar circuit for detecting when there is too little light comprises an OSM 50, a coincidence gate 51, an inverter 52, a Nand gate 53, a flip-flop 54, and an indicator 55. Here, the time duration T2 of the output of OSM 50 is set for a longer period of time indicative of a lower light intensity and the pulses S1 and S2 will have a lesser repetition rate due to the fact that the sensed light intensity will be lower. OSM 50 is connected to fire on the trailing edge of the start scan pulses. When the system is operating within its designed parameters, a suceeding start pulse S2 (FIG. 6b) after a preceding start pulse S1 will occur during the time duration T2 of the output of OSM 50.

The output of gate 51, a coincidence gate, will set flip-flop 54 when the succeeding start pulse occurs during the time T2 set by the preceding start pulse, FIG. 6b. This indicates that adequate light is present. Gate 53 will not pass a reset signal to flip-flop 54 if the succeeding start pulse S2 occurs during the duration of time T, and thus flip-flop 54 will not be reset so long as the light intensity is above point D, FIG. 5. Indicator 55 may be alternatively arranged to give an illuminated signal if the light intensity drops below the point D. In this manner, through viewing the indicators 45 and 55, a determination may be made that the light intensity is in the range between the points D and E on the curves of FIG. 5. If there should be an indication that there is insufficient light intensity on the diodes, then the aperture of the lens may be opened to permit entrance of more light, or in the reverse case the background light may be increased.

The network of FIG. 5 in essence compares the time of occurrence of the start scan signal S with the termination of the two timing periods T1 and T2 to monitor the intensity of the light. The foregoing description of the invention assumes a unity object to image ratio or unity magnification by lens 20. If this is not the case, suitable ratio factors may be introduced into the indicator 26.

In this manner, the sufficiency of the light intensity may be monitored, or otherwise stated, the range of sufficient light intensity may be monitored and indicated.

A typical array may include 1024 diodes spaced 0.001" or 0.002" on centers and a 1024 bit shift register. The shift register acts as a gating or interrogating device. A scan cycle is fixed in time for a given array by the clock frequency. However, the repetition rate of the scan cycles is determined by sensed light intensity.

While preferred embodiments of the invention have been set forth for purposes of disclosure, modifications to the disclosed embodiments as well as other embodiments thereof may occur to those skilled in the art. Accordingly, the appended claims are intended to cover all embodiments which do not depart from the spirit and scope of the invention.

What is claimed is:

1. In an apparatus for gating the thickness of strip material comprising a linear array of back-biased photo-sensitive electrically conductive elements, means for imaging the strip across said array, each of said elements having a capacitance which may discharge through the element at a rate dependent on the light intensity incident thereon and a switch in circuit with each element for completing a circuit therethrough, means for sequentially closing and then opening said switches to recharge said capacitances in a cycle of operation, means for counting the charging pulses during a cycle of operation; separate photo-sensitive means for sensing the light from one of said strip and the background, means responsive to said separate means for generating pulses at a repetition rate proportional to the intensity of light from said one of said strip and the background, and means for utilizing said pulses to commence a cycle of operation of sequentially closing said switches, whereby the time between cycles of operation is regulated as a function of the light intensity sensed by said separate means.

2. The apparatus of claim 1 further including a clock pulse generator for generating clock pulses at a predetermined rate, the clock pulses being sequentially applied to operate said switches through an address register upon occurrence of the light intensity proportional pulse.

3. The apparatus of claim 1 further including means for monitoring the light intensity sensed by said generating means between predetermined limits.

4. The apparatus of claim 3 wherein said further means comprises first and second means for generatig first and second timing signals in response to initiation of a cycle of operation and means for indicating when the initiation of a succeeding cycle occurs in predetermined timed relation to the timing signals.

5. In an apparatus for gaging the thickness of strip material comprising a linear array of back-biased photo-sensitive electrically conductive elements, means for imaging the strip across said array, each of said elements having a capacitance which may discharge through the element at a rate dependent on the light intensity incident thereon, and a switch in circuit with each element for completing a circuit therethrough to means for sequentially closing and then opening said switches to charge said capacitances in a cycle of operation, means for counting the charging pulses during a cycle of operation whereby the thickness of the material is determined from the number of charging pulses; means for generating a start cycle signal as a function of the light intensity from one of the strip and the background, means responsive to said start cycle signal for indicating that the intensity of light on said array elements is within predetermined limits.

6. The apparatus of claim 5 wherein said means responsive to said start cycle signal comprises first and second timing means each generating first and second timing signals of predetermined duration, and means for comparing the time of occurrence of the start cycle signal with termination of said first and second timing signals.

* * * * *

UNITED STATES PATENT AND TRADEMARK OFFICE
CERTIFICATE OF CORRECTION

PATENT NO. : 4,160,599
DATED : July 10, 1979
INVENTOR(S) : JOSEPH L. SPERRAZZA

It is certified that error appears in the above-identified patent and that said Letters Patent are hereby corrected as shown below:

Column 1, line 20, after "problem", delete the comma.

Column 2, line 43, "curent" should read --current--.

Column 2, line 59, "supplied" should read --applied--.

Column 5, line 1 of claim 1, "gating" should read --gaging--.

Column 6, lines 2 and 3 of claim 3, "generating" should read --separate--.

Column 6, line 1 of claim 4, "wherein" should read --where--.

Signed and Sealed this

Ninth Day of October 1979

[SEAL]

Attest:

RUTH C. MASON
Attesting Officer

LUTRELLE F. PARKER
Acting Commissioner of Patents and Trademarks